US009745232B2

United States Patent
Pigourier et al.

(10) Patent No.: US 9,745,232 B2
(45) Date of Patent: Aug. 29, 2017

(54) PROCESS FOR THE ISOMERIZATION OF C5/C6 HYDROCARBON CUTS WITH CHLORINATED COMPOUND RECYCLING

(71) Applicant: AXENS, Rueil Malmaison (FR)

(72) Inventors: Jerome Pigourier, Meudon (FR); Isabelle Prevost, Rueil Malmaison (FR); Laurent Watripont, Nanterre (FR); Pierre-Yves Martin, Rueil Malmaison (FR)

(73) Assignee: AXENS, Rueil-Malmaison (FR)

( * ) Notice: Subject to any disclaimer, the term of this patent is extended or adjusted under 35 U.S.C. 154(b) by 86 days.

(21) Appl. No.: 14/886,912

(22) Filed: Oct. 19, 2015

(65) Prior Publication Data

US 2016/0107954 A1   Apr. 21, 2016

(30) Foreign Application Priority Data

Oct. 20, 2014   (FR) ..................... 14 60090

(51) Int. Cl.
| | |
|---|---|
| *C07C 7/11* | (2006.01) |
| *C07C 5/27* | (2006.01) |
| *C10G 35/04* | (2006.01) |
| *C10G 45/60* | (2006.01) |

(52) U.S. Cl.
CPC .......... *C07C 5/2772* (2013.01); *C07C 5/2791* (2013.01); *C07C 7/11* (2013.01); *C10G 35/04* (2013.01); *C10G 45/60* (2013.01); *C07C 2521/04* (2013.01); *C07C 2523/42* (2013.01); *C07C 2527/06* (2013.01)

(58) Field of Classification Search
CPC .......... C07C 5/2772; C07C 7/11; C10G 35/04
See application file for complete search history.

(56) References Cited

U.S. PATENT DOCUMENTS

| | | | |
|---|---|---|---|
| 2,406,778 A | 9/1946 | Kruse et al. | |
| 2,414,371 A | 1/1947 | Fragen et al. | |
| 3,188,361 A * | 6/1965 | Cabbage ............... | C07C 5/2253 422/107 |
| 4,275,257 A * | 6/1981 | Hutson, Jr. ........... | C07C 5/2789 585/372 |

OTHER PUBLICATIONS

Search Report for FR1460090 dated Jun. 9, 2015.

* cited by examiner

*Primary Examiner* — Sharon Pregler
*Assistant Examiner* — Alyssa L Cepluch
(74) *Attorney, Agent, or Firm* — Millen, White, Zelano & Branigan, P.C.

(57) ABSTRACT

A process for the isomerization of a feed of hydrocarbon compounds containing $C_5$ and/or C hydrocarbon compounds, comprising: a) supplying an isomerization unit with at least one liquid fraction of the feed of hydrocarbon compounds and isomerizing the feed in the presence of a chlorinated catalyst; b) supplying a stabilization unit containing at least one stabilization column with the effluent obtained from the isomerization unit and separating the effluent; c) providing an absorption unit having one absorption column; d) extracting a liquid flow enriched in chlorinated compounds from the absorption unit which is recycled to the isomerization unit; and e) extracting the liquid flow containing at least one isomerate from the stabilization unit.

13 Claims, 5 Drawing Sheets

PROCESS FOR THE ISOMERIZATION OF C5/C6 HYDROCARBON CUTS WITH CHLORINATED COMPOUND RECYCLING

TECHNICAL FIELD

The present invention concerns the field of processes for the isomerization of hydrocarbon cuts, and more particularly of cuts comprising paraffins containing 5 and 6 carbon atoms, and possibly comprising paraffins containing 4 and/or 7 or even 8 carbon atoms.

PRIOR ART

The octane number of $C_5$ and $C_6$ type hydrocarbon cuts obtained from the distillation of crude oil is generally in the range 60 to 75, i.e. much lower than regulations in force; in Europe, the octane number specifications for gasoline are set at 95 or higher. The process generally used to increase the octane number of $C_5$ and $C_6$ cuts consists of isomerization of normal paraffin compounds (n-paraffins) with a low octane number to branched paraffins with a high octane number.

Many processes are known for the isomerization of hydrocarbon cuts containing 5 to 6 carbon atoms and typically containing a majority of paraffins. Typically, the isomerization units comprise acid catalysts which can be used to form carbo-cations which are recognized as being intermediate active species. The catalysts which are the most widely used industrially comprise at least one noble metal such as platinum deposited on a support, generally chlorinated alumina (approximately 5% to 10% by weight of chlorine). The stability and activity of catalysts of this type are maintained by injecting a chlorinating agent, precursors of hydrochloric acid, in order to keep the chlorine content of the catalyst constant. However, the presence of chlorine on the catalyst is not without its disadvantages. In fact, over time, an elution of chlorine, in particular in the form of hydrogen chloride, may be observed. Thus, this elution means that the catalyst must be constantly recharged with chlorine. It also results in the presence of hydrogen chloride and/or other chlorinated compounds in the gaseous and liquid effluents obtained from the isomerization unit, which inevitably leads to a problem with corrosion of the facilities, to a problem with the formation of deposits or salts based on chlorine, or even to a problem with the accelerated contamination of the catalysts which might be located downstream of the isomerization unit. Thus, it is important to eliminate all traces of hydrogen chloride or chlorinated compounds from these effluents.

Patent GB 572 697 describes the recovery of hydrogen chloride, used as a catalytic promoter in the effluents from a unit for the isomerization of normal $C_4$ or $C_5$ paraffins by bringing them into contact with a metallic sulphate type solid such as copper or zinc sulphate, for example. The chlorinated compounds are then recovered by raising the temperature.

Patents GB 578 085, U.S. Pat. No. 3,188,361 and U.S. Pat. No. 4,275,257 have also proposed recovering the chlorinated compounds contained in the effluents from reactors for the isomerization of $C_4$ to $C_6$ paraffins using stripping steps preceded or followed by absorption steps. Those processes use soluble isomerization catalysts comprising a metallic halide, such as aluminium or zinc chloride, and hydrogen chloride (HCl), necessitating the recovery of significant quantities of hydrogen chloride introduced into the reactor to recycle them.

Isomerization processes are also known which use catalysts based on chlorinated alumina and platinum, the chlorinated products of which are sent to a purification device (also known as a scrubber) for neutralization. A device of that type has in particular been described in the document U.S. Pat. No. 4,804,803.

However, the prior art units for recycling chlorinated compounds comprising an absorption of chlorine contained in the flow directed towards the purification device by a washing liquid which can be upgraded (feed or product of the unit) operate to the detriment of the overall yield of the compounds with a high octane number.

One aim of the invention is to propose a novel process for the isomerization of paraffins which can overcome the disadvantages mentioned above, while providing for a high yield of products comprising a high octane number to be obtained.

The process of the invention is distinguished from prior art processes in that it can be used to increase the overall yield of compounds comprising a high octane number, while maintaining an identical recycle ratio for the chlorinated compounds.

AIMS OF THE INVENTION

In general, the invention concerns a process for the isomerization of a feed of hydrocarbon compounds comprising $C_5$ and/or $C_6$ hydrocarbon compounds, said process comprising a loop for recycling at least one chlorinated compound, and in which process:

a) an isomerization unit is supplied with at least one liquid fraction of said feed of hydrocarbon compounds and the isomerization is carried out in the presence of a chlorinated catalyst;

b) a stabilization unit comprising at least one stabilization column is supplied with the effluent obtained from the isomerization unit and a separation is carried out in said stabilization unit into:
   - a gaseous effluent comprising at least one chlorinated compound;
   - a liquid effluent comprising a concentration $C_A$ of $C_{5+}$ compounds; and
   - a liquid flow comprising at least one isomerate of the feed of hydrocarbon compounds;

c) the following is carried out in an absorption unit comprising at least one absorption column:
   - a first contact between the gaseous effluent obtained from step b) and a washing fluid, said washing fluid being selected from a complementary liquid fraction of said feed and/or at least a portion of said liquid flow comprising at least one isomerate of the feed of hydrocarbon compounds obtained from step b); said washing fluid comprising a concentration $C_B$ of $C_{5+}$ compounds, with $C_A < C_B$;
   - a second contact between the gaseous flow resulting from said first contact and said liquid effluent obtained from step b);

d) a liquid flow enriched in chlorinated compounds is extracted from the absorption unit and returned to the isomerization unit;

e) said liquid flow comprising at least one isomerate of the feed of hydrocarbon compounds is extracted from the stabilization unit.

Advantageously, the liquid flow comprising at least one isomerate of the feed of hydrocarbon compounds of step e) undergoes a separation in a separation unit in order to obtain at least one flow with a higher octane number than said liquid flow of step e) and at least one flow with a lower octane number than said liquid flow of step e).

More particularly, at least a portion of the flow with a lower octane number than said liquid flow of step e) is recycled to the absorption unit as washing fluid.

Advantageously, at least a portion of the flow with a lower octane number than said liquid flow of step e) is recycled upstream of the isomerization unit, said recycled flow being mixed with the feed of hydrocarbon compounds.

More precisely, the absorption unit comprises an absorption column, and during step c), said absorption column is supplied:

with said washing fluid;
with gaseous effluent obtained from step b), said gaseous effluent being supplied to the absorption column below the supply for said washing fluid;
with liquid effluent obtained from step b), said liquid effluent being supplied to the head of the absorption column above said washing fluid.

In another embodiment of the process of the invention, the absorption unit comprises two absorption columns, and during step c), the washing fluid and the gaseous effluent obtained from step b) are supplied to the first absorption column, and the gaseous flow resulting from the first contact between the gaseous effluent obtained from step b) and said washing fluid and the liquid effluent obtained from step b) are supplied to the second absorption column.

Preferably, said feed of hydrocarbon compounds, optionally as a mixture with said liquid flow comprising at least one isomerate of the feed of hydrocarbon compounds obtained from step b), is dried upstream of the isomerization unit and the absorption unit.

Advantageously, the washing fluid is cooled upstream of the absorption unit.

According to the invention, when the washing fluid is a complementary liquid fraction of said feed, the flow rate of said complementary liquid fraction of said feed is preferably in the range 5% to 50% by volume of the total flow of said feed.

Preferably, the concentration of $C_{4-}$ compounds comprised in the liquid effluent obtained in step b) is more than 15% by weight.

Advantageously, the gaseous flow obtained from the second contact in the absorption unit is extracted and treated in a unit for the treatment of gaseous effluents.

Advantageously, a portion of the liquid effluent obtained from step b) is sent directly to a unit for the treatment of gaseous effluents following vaporization.

More precisely, step a) is carried out at a temperature in the range 100° C. to 300° C., at a pressure in the range 0.2 to 3.5 MPa, with a hydrogen/hydrocarbons molar ratio in the range 0.1:1 to 1:1 and with a space velocity in the range 0.5 to 10 h$^{-1}$.

Preferably, step a) is carried out in the presence of a chlorinated catalyst comprising an alumina support and a metal from group VIII. Preferably, the catalyst comprises 2% to 10% by weight of chlorine with respect to the total catalyst weight, and 0.1% to 0.40% by weight of platinum with respect to the total catalyst weight.

In a variation, the invention concerns a process for the isomerization of a feed of hydrocarbon compounds comprising $C_5$ and/or $C_6$ hydrocarbon compounds, said process comprising a loop for recycling at least one chlorinated compound, and in which process:

a') an isomerization unit is supplied with at least one liquid fraction of said feed of hydrocarbon compounds and the isomerization is carried out in the presence of a chlorinated catalyst;

b') a stabilization unit comprising at least one stabilization column is supplied with the effluent obtained from the isomerization unit and a separation is carried out in said stabilization unit into:
   a gaseous effluent comprising at least one chlorinated compound;
   a liquid effluent comprising a concentration $C_A$ of $C_{5+}$ compounds; and
   a liquid flow comprising at least one isomerate of the feed of hydrocarbon compounds;

c') the following is carried out in an absorption unit comprising at least one absorption column:
   a first contact between the gaseous effluent obtained from step b') and a washing fluid, said washing fluid being selected from a complementary liquid fraction of said feed and/or at least a portion of a flow enriched in compounds with a low octane number obtained from step e); said washing fluid comprising a concentration $C_B$ of $C_{5+}$ compounds, with $C_A<C_B$;
   a second contact between the gaseous flow resulting from said first contact and said liquid effluent obtained from step b');

d') a liquid flow enriched in chlorinated compounds is extracted from the absorption unit and returned to the isomerization unit;

e') said liquid flow comprising at least one isomerate of the feed of hydrocarbon compounds from step b') undergoes a separation in a separation unit in order to obtain at least one flow with a higher octane number than said liquid flow from step b') and at least one flow with a lower octane number than said liquid flow from step b').

DETAILED DESCRIPTION OF THE INVENTION

Definitions

The term "chlorinated compound" as used in the present invention means any liquid or gaseous compound comprising one or more chlorine atoms.

The term "$C_{n+}$ hydrocarbon cut" means a cut comprising hydrocarbons containing n carbon atoms.

The term "$C_{n+}$ cut" means a cut comprising hydrocarbons containing at least n carbon atoms.

The term "$C_{n-}$ cut" means a cut comprising hydrocarbons containing at most n carbon atoms.

The term "washing fluid" as used in the context of the invention means either a liquid fraction which is complementary to the (fresh) feed of hydrocarbon compounds, or at least a portion of a liquid flow comprising at least one isomerate of the feed of hydrocarbon compounds, preferably a flow with a lower octane number than the liquid flow comprising at least one isomerate obtained by separation of said fluid comprising at least one isomerate, or indeed a mixture of feed and flow comprising an isomerate.

The term "recycled flow" means at least a portion of a liquid flow comprising at least one isomerate of the feed of hydrocarbon compounds, preferably a flow with a lower octane number than the liquid flow comprising at least one isomerate obtained by separation of said flow comprising at least one isomerate.

The term "mono-branched" and "di-branched" as used in the invention respectively mean compounds with one branch, or a tertiary carbon, and two branches, comprising either two tertiary carbon atoms or a quaternary carbon atom.

In the context of the invention, the terms "upstream" and "downstream" are defined with respect to the direction of flow of the feed of hydrocarbon compounds, possibly mixed with a recycled flow.

Detailed Description

Processes for the isomerization of cuts usually comprising paraffins containing 5 and 6 carbon atoms and which may optionally comprise paraffins containing 4 and/or 7 or even 8 carbon atoms are known to the skilled person. The feeds used in the process of the invention generally comprise between 25% and 100% by weight of paraffins, more particularly between 25% and 100% by weight of normal paraffins, and still more particularly between 30% and 60% by weight of normal $C_5$ and $C_6$ paraffins.

These processes generally use a catalyst selected from three different known types of catalyst: Friedel-Crafts type catalysts, bifunctional zeolitic catalysts comprising a metal from group VIII deposited on zeolite, and bifunctional metal/support catalysts based on metals from group VIII deposited on alumina, typically platinum, and generally containing a halogen, for example chlorine. The isomerization process of the invention is preferably operated in the presence of a catalyst based on chlorinated alumina and platinum. Typically, the isomerization process is operated at low temperature, for example in the range 100° C. to 300° C., preferably in the range 110° C. to 240° C., at high pressure, for example in the range 0.2 to 3.5 MPa, and with a hydrogen/hydrocarbons molar ratio in the range 0.1:1 to 1:1, and with a space velocity in the range 0.5 to 10 $h^{-1}$, preferably in the range 1 to 4 $h^{-1}$.

The known catalysts used in the isomerization processes are preferably constituted by an alumina support preferably comprising 2% to 10% by weight of chlorine with respect to the total weight of catalyst, and 0.1% to 0.40% by weight of platinum with respect to the total weight of catalyst.

Maintaining the level of chlorination of the catalyst generally necessitates the continuous addition of a chlorinated compound such as carbon tetrachloride, injected as a mixture with the feed of hydrocarbon compounds, typically at a concentration in the range 50 to 600 parts per million by weight into the flow entering the reactor or reactors of the isomerization unit which comprise the catalyst.

Figure 1A:
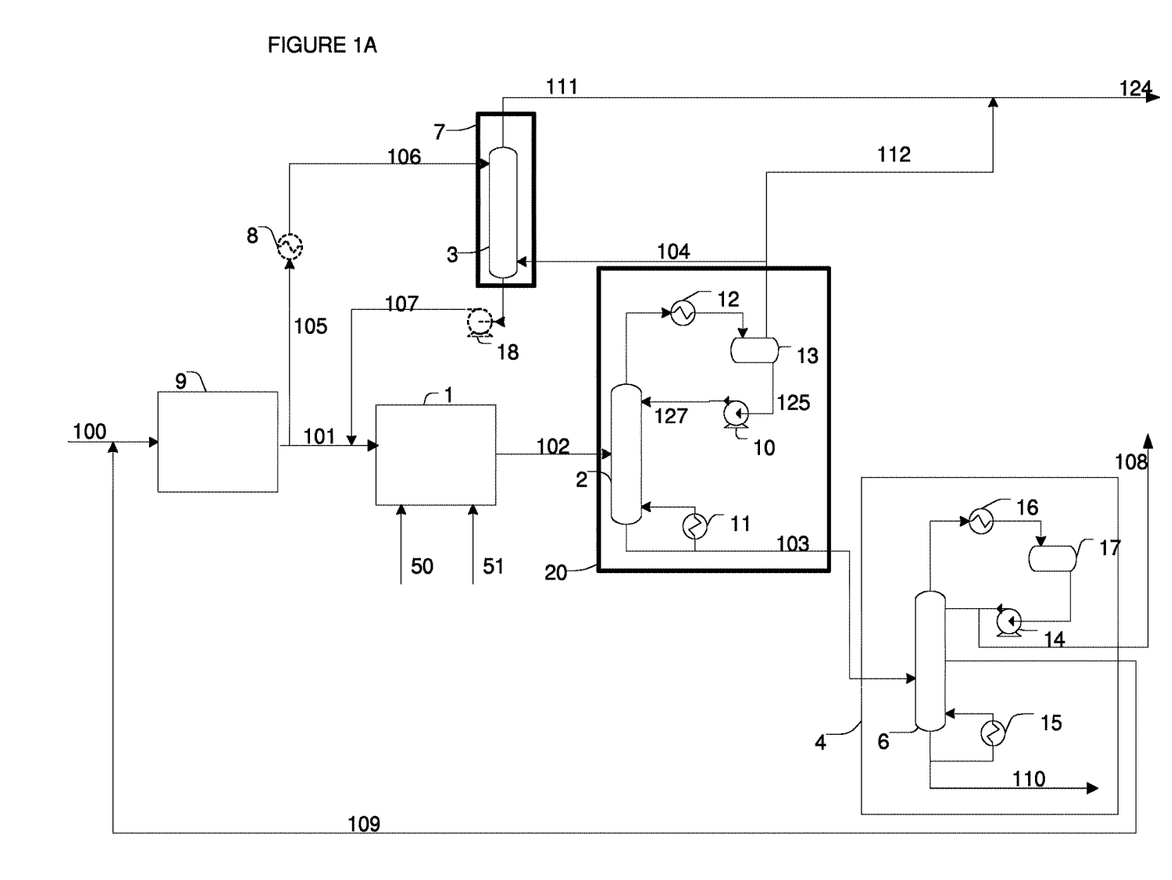
FIGS. 1a, 1b and 1c diagrammatically represent an industrial facility for carrying out a process for the isomerization of hydrocarbon compounds which is known in the art. The plant comprises a reaction section 1 (also known here as an isomerization unit), a stabilization unit 20, an absorption unit 7 and a separation unit 4.
Figure 1B:
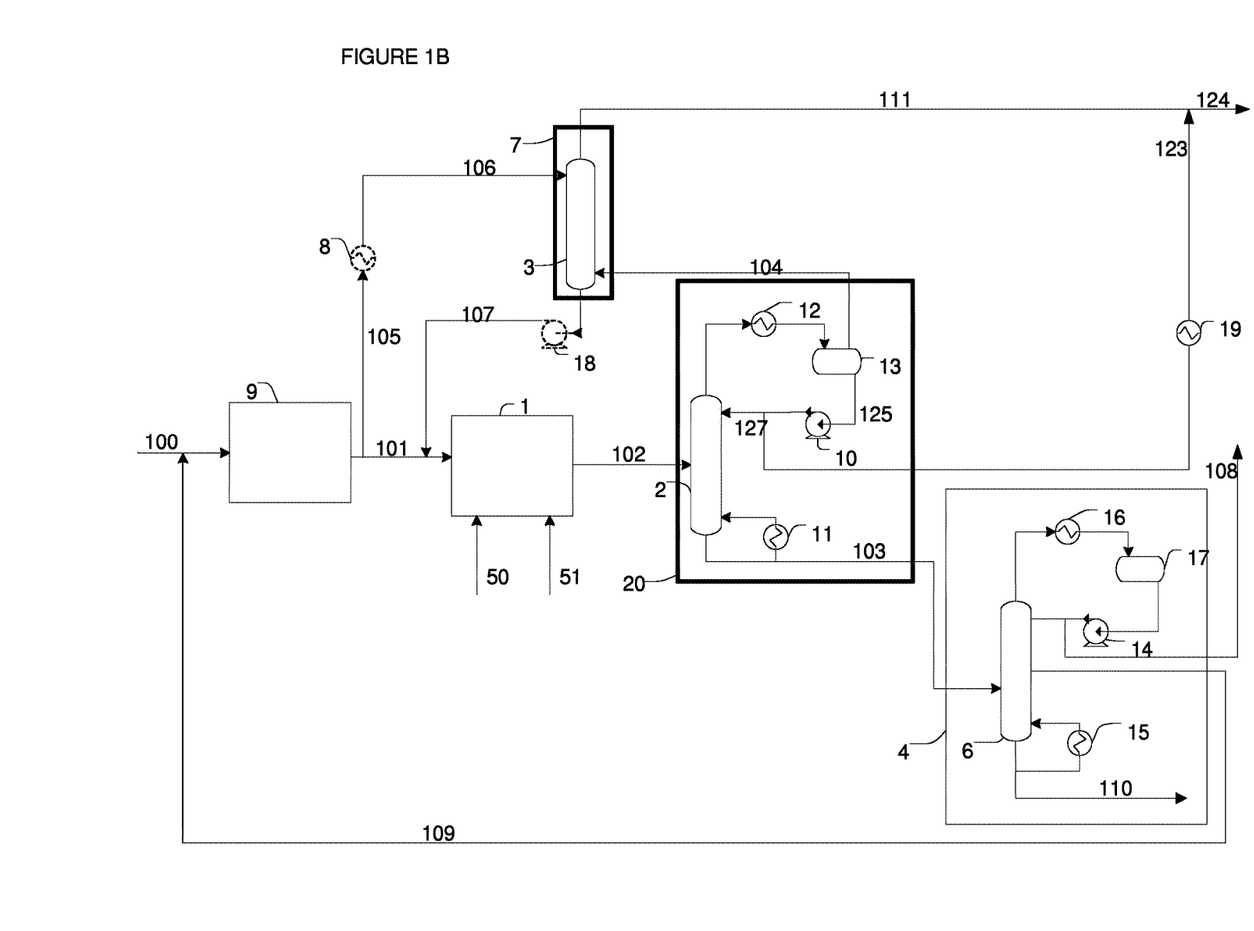
Figure 1C:
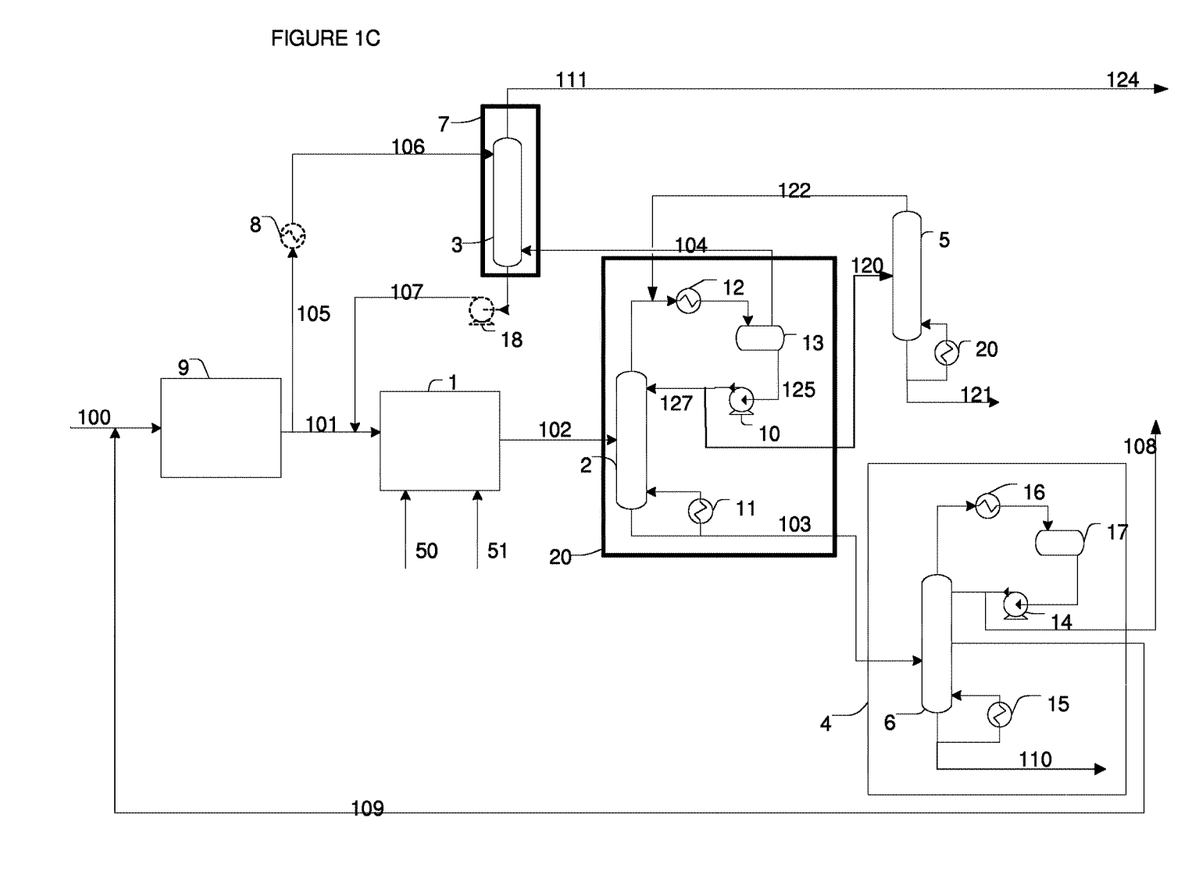
Figure 2A:
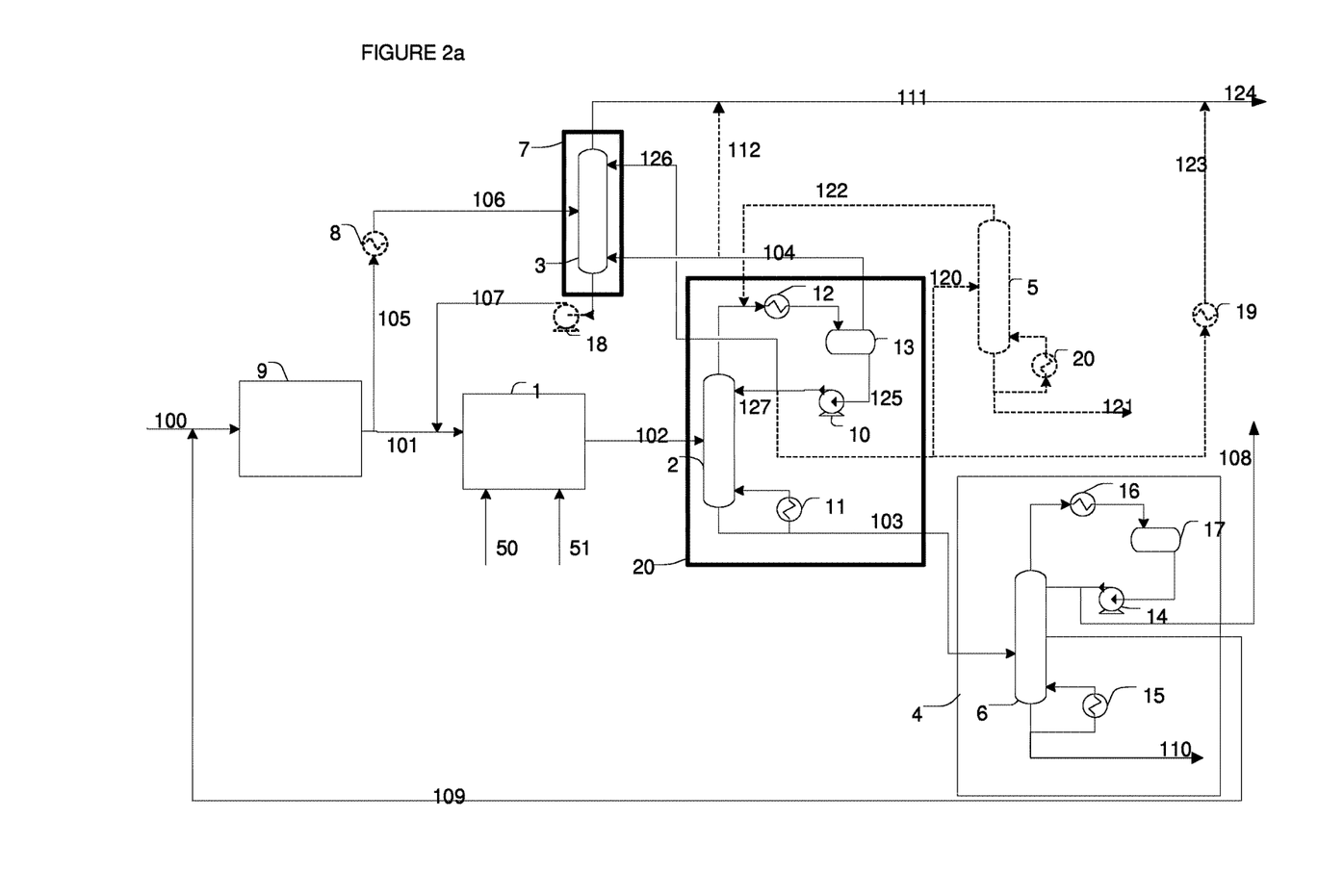
FIG. 2a is a diagrammatic representation of an industrial facility for carrying out the isomerization process of the invention.
Figure 2B:
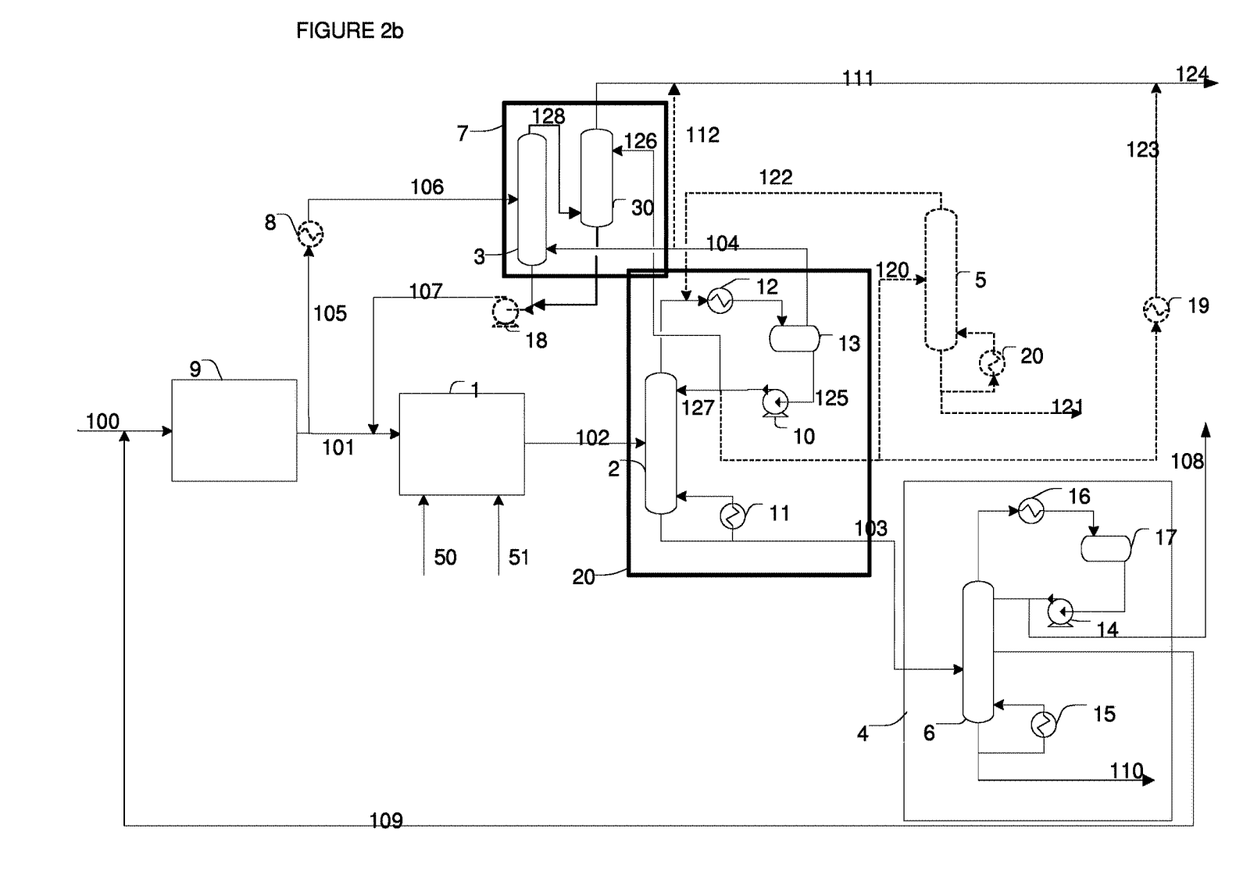
FIG. 2b is a diagrammatic representation of a variation of the process of the invention.

In the description below, firstly, a prior art isomerization process (as represented in FIGS. 1a, 1b and 1c) will be described, then secondly, an isomerization process in accordance with the invention (as represented in FIGS. 2a and 2b).

Referring to FIGS. 1a, 1b and 1c, a feed of hydrocarbon compounds, in particular hydrocarbon compounds of the $C_5$ and $C_6$ type, is directed into the isomerization process via a conduit 100 and is optionally mixed with recycled products originating from line 109. The recycling products will be described in the description below. The mixture is then dried in the vessel 9. Drying is generally carried out by adsorption over a molecular sieve.

The dry flow obtained from mixing the feed of hydrocarbon compounds possibly comprising recycled products is then split into two fractions. A first liquid fraction of a feed of hydrocarbon compounds is directed directly towards the isomerization reaction section 1 via the line 101, and a second fraction (also known here as the complementary liquid fraction of the feed of hydrocarbon compounds) is supplied to an absorption unit 7 comprising an absorption column 3 via the lines 105 and 106. The complementary liquid fraction may be cooled using a heat exchanger 8. This second fraction is known as the washing fluid. In this embodiment, the washing fluid is constituted by the complementary liquid fraction of the feed of hydrocarbon compounds. Hydrogen is supplied to the reaction section 1 by means of the flow 50 and chlorinated compounds are supplied to the reaction section 1 by means of the flow 51.

The effluent obtained from the isomerization reaction section 1 is sent to a stabilization unit 20 comprising a stabilization column 2 via the line 102. The stabilization column 2 can be used to eliminate the lightest compounds from the column head, i.e. methane, ethane, propane, butane, to eliminate excess hydrogen as well as hydrochloric acid and/or chlorinated compounds originating from the isomerization catalyst. The gaseous effluent from the head of the stabilization column 2 is then cooled using the condenser 12 and is sent to a reflux drum 13. The gaseous effluent from the reflux drum 13 is sent to the bottom of the absorption column 3 via the line 104. The liquid effluent from the reflux drum 13 is re-injected to the head of the stabilization column via the lines 125 and 127 and by means of the pump 10.

In the absorption column 3, contact of the gaseous effluent obtained from the head of the stabilization column 2 and the reflux drum 13 (via the line 104) with the washing fluid (via the lines 105 and 106) means that a portion of the hydrochloric acid and/or chlorinated compounds contained in the gaseous effluent can be recovered. This recovery means that the quantity of hydrochloric acid in the gaseous flow from the head of the absorption column 3 can be reduced; this gaseous flow is then sent to a unit for the treatment of gaseous effluents, for example a unit for neutralization with sodium hydroxide (not shown in FIG. 1), via the lines 111 and 124 (see FIG. 1). Thus, the costs associated with treatments of gaseous effluents charged with hydrochloric acid is reduced, meaning, for example, a lower consumption of sodium hydroxide and, as a consequence, a smaller quantity of salts produced during neutralization.

The washing fluid which has been used in the absorption column 3 is principally recovered from the bottom of the column and is mixed, via the line 107 and optionally by means of a pump 18, with the rest of the feed of hydrocarbon compounds and any recycling products. The hydrochloric acid which is entrained thereby is recycled to the isomerization reaction section 1, which further reduces the quantity of additional chlorinated compounds which has to be added to said isomerization unit.

However, a major disadvantage of this isomerization process resides in the fact that the portion of light compounds such as methane, ethane, propane and butane present in the gaseous effluent from the head of the stabilization column 2 are also re-entrained with the washing fluid and are thus recycled to the reaction section of the isomerization unit 1 which, in the absence of any means for purging them, could cause an unacceptable accumulation of these compounds.

As can be seen in FIG. 1a, a prior art solution to this problem was to send, via the line 112, a portion of the gaseous effluent from the stabilization column 2 directly for treatment without passing through the absorption column 3. The problem is to reduce the level of HCl recycling.

Another prior art solution for overcoming this problem was to withdraw a liquid distillate from the reflux drum 13 of the stabilization column 2. This liquid distillate, the quantity of which depends on the quantity of light products, may be:

either sent directly to the step for treatment of the effluents from the absorption column 3 after vaporization in an exchanger 19 (represented by the line 123) as represented in FIG. 1b;

or directed via the conduit 120 to a second stabilization column 5, as can be seen in FIG. 1c, the overhead flow from the stabilization column 5 being directed to the condenser 12 of the stabilization column 2 via the line 122. The bottom flow from the stabilization column 5, essentially reboiled in the reboiler 20, is removed via the conduit 121 and constitutes a product of the process. This product essentially comprises liquefied petroleum gas (LPG) which can be upgraded and has a hydrochloric acid content which is generally compatible with the required specifications, but may sometimes necessitate a supplemental purification step using a chlorine capture process, for example by adsorption.

The bottom of the stabilization column 2 from which the hydrochloric acid has been eliminated, constituting the process product (isomerate), is recovered via the line 103 and comprises one or more products enriched in compounds with a high octane number. This latter has a research octane number which is higher than the octane number of the feed of hydrocarbon compounds upstream of the isomerization unit. It may constitute a high octane number gasoline. A fraction of the bottom flow from the stabilization column 2 is reheated via the reboiler 11 and is returned to the bottom of said stabilization column 2.

This product may also undergo a supplemental separation step 4 in which on the one hand, one or more fluids enriched in compounds with a low octane number are recovered and recycled to the reaction section via the conduit 109, and on the other hand one or more products enriched in compounds with a high octane number are obtained from lines 108 and 110. To this end, at least a portion of the bottom flow from the stabilization column 2 is sent to a separation unit 4, for example a distillation column 6, via the line 103. Said flow may also be separated using any other means, for example by a stabilization column, or even an adsorption column. The overhead flow from column 6 is cooled by the condenser 16 and sent to the reflux drum 17. A portion of the liquid effluent obtained from the reflux drum 17 is re-injected to the head of the distillation column 6 as a reflux via a pump 14; the complementary portion of the liquid effluent obtained from the reflux drum 17 is recovered via the pump 14 and the line 108, and comprises products enriched in compounds with a high octane number. A flow enriched in compounds with a high octane number and with refractory naphthenic $C_{6+}$ compounds is recovered from the bottom of the distillation column 6 via the line 110 and is thus purged to prevent them from accumulating. A portion of the bottom flow is reheated in a reboiler 15 and returned to the bottom of said distillation column 6.

Advantageously, the washing fluid sent to the absorption column 3 via the lines 105 and 106 may be cooled in advance using an exchanger 8 in order to improve the degree of recovery of the hydrochloric acid. Preferably, washing is carried out at low temperature in order to improve the washing efficiency; more particularly, it is carried out at ambient temperature.

However, during washing of the overhead gaseous effluent from the stabilization column 2 in the prior art processes, inevitably, a loss of compounds containing five carbon atoms or more ($C_{5+}$) occurs, but these are eminently upgradable, which inevitably leads to an overall reduction in the isomerization process yield. In fact, in prior art processes, contact between the gaseous effluent from the reflux drum 13 and the complementary liquid fraction of the feed of hydrocarbon compounds also sent to the absorption unit 7 via the line 106 forms a gaseous flow comprising $C_{5+}$ compounds. The $C_{5+}$ compounds included in the gaseous flow obtained from this contact are then entrained towards the gaseous effluent treatment unit via the lines 111 and 124, and thus cannot be recovered. Hence, in contrast to the recovery of chlorinated compounds originating from the isomerization unit 2 via the line 104, the $C_{5+}$ compounds obtained from the liquid fraction of the feed of hydrocarbon compounds are entrained, which reduces the overall yield of the process for the isomerization of hydrocarbon compounds.

The process of the invention can be used to avoid recycling unwanted products in a loop, such as the lightest compounds, while optimizing recycling of hydrochloric acid and/or chlorinated compounds, and at the same time avoiding a loss of hydrocarbon compounds which can be upgraded into products, more particularly $C_{5+}$ compounds.

In accordance with the invention, in order to avoid a loss of yield of upgradable hydrocarbon compounds, i.e. the $C_{5+}$ compounds, the gaseous flow obtained from contact between the gaseous effluent from the reflux drum 13 sent via the line 104 to the absorption unit 7 and the complementary liquid fraction of the feed of hydrocarbon compounds sent to the absorption unit 7 via the line 106 is contacted with the liquid effluent from the reflux drum 13 injected into the absorption unit 7 via the line 126. In fact, the liquid effluent from the reflux drum 13 injected into the absorption unit 7 via the line 126 comprises a smaller quantity of $C_{5+}$ compounds than the concentration of $C_{5+}$ compounds of the complementary fraction of the feed of hydrocarbon compounds. Thus, the $C_{5+}$ compounds contained in the gaseous effluent obtained from the first contact condense in contact with the liquid effluent from the reflux drum 13 injected into the absorption unit 7 via the line 126.

More generally, in order to increase the yield of $C_{5+}$ compounds from the isomerization process of the invention, the concentration "$C_A$" of $C_{5+}$ compounds of the liquid effluent obtained from the stabilization unit 20, sent to the absorption unit 7, must be less than the concentration "$C_B$" of the $C_{5+}$ compounds of the complementary liquid fraction of the feed of hydrocarbon compounds sent to the absorption unit 7.

Advantageously, the concentration of $C_{4-}$ compounds present in the liquid effluent obtained from the stabilization unit 20 injected into the absorption unit 7 is more than 15% by weight, and still more preferably more than 30% by weight.

Referring now to FIGS. 2a and 2b (in these figures, identical references to those of FIGS. 1a to 1c designate identical elements), which represent two possible and non-limiting embodiments of the process of the invention, a feed of hydrocarbon compounds, in particular hydrocarbon compounds of the $C_5$ and $C_6$ type, is directed to the isomerization process via a conduit 100 and is optionally mixed with a recycled flow comprising recycling products originating from line 109.

The step for drying the fresh feed may be carried out upstream or downstream of mixing between said feed and the recycled products obtained from the flow in line 109. In a preferred embodiment, drying is carried out downstream of said mixing in a manner such as to eliminate any presence of water which may be susceptible of being supplied via the recycled products line 109.

The dry flow obtained from mixing the feed of hydrocarbon compounds, optionally mixed with the recycled flow, is then split into two fractions. A first fraction is directed directly towards the isomerization reaction section via the line 101, and a second fraction (washing fluid) is supplied to an absorption unit 7 via the lines 105 and 106. In the context of the process of the invention, the rate of flow of washing fluid is in the range 5% to 50% by volume of the total rate of flow of the feed of hydrocarbon compounds, optionally mixed with a recycled flow, preferably between 10% and 30% by volume.

In a particular embodiment of the process of the invention (not shown in the figures), it is possible to split the feed of hydrocarbon compounds before mixing with the recycled flow obtained from the line 109 and sending only a fraction of the feed of hydrocarbon compounds towards the absorption unit 7, in the absence of recycled flow.

In another particular embodiment of the process of the invention (not shown in the figures), it is possible to send only a fraction of recycled flow obtained from the line 109 towards the absorption unit 7, in the absence of a feed of hydrocarbon compounds. In this embodiment, the washing fluid is the recycled flow, i.e. the flow having a lower octane number than the liquid flow comprising at least one isomerate of the feed of hydrocarbon compounds.

In yet another particular embodiment of the process of the invention (not shown in the figures), the washing fluid is constituted by a mixture of a fluid comprising the complementary liquid fraction of said feed of hydrocarbon compounds and recycled flow.

As can be seen in FIG. 2a, the effluent from the isomerization reaction section 1 is sent towards the stabilization column 2 via the line 102, allowing the lightest compounds to be eliminated from the column head, i.e. methane, ethane, propane, butane, allowing excess hydrogen to be eliminated, as well as hydrochloric acid and/or chlorinated compounds originating from the catalyst. The gaseous effluent from the head of the stabilization column 2 is then cooled by means of a condenser 12 and is sent to a reflux drum 13. The gaseous effluent from the reflux drum 13 is sent via the line 104 to the bottom of the absorption unit 7 comprising an absorption column 3. A portion of the liquid effluent from the reflux drum 13 is re-injected as a reflux to the head of the stabilization column 2 via the lines 125 and 127, optionally by means of the pump 10.

In the absorption column 3, contact of the gaseous effluent obtained from the head of the stabilization column 2 (via the line 104) by the washing fluid (via the lines 105 and 106) means that a portion of the hydrochloric acid and/or chlorinated compounds contained in the gaseous effluent can be recovered. This recovery means that the quantity of hydrochloric acid in the effluent from the head of the absorption column 3 can be reduced, this effluent then being sent to a unit for the treatment of gaseous effluents (not shown in FIG. 1) via the line 111.

The term "hydrochloric acid recovery ratio" means the ratio between the flow rate of hydrochloric acid of the bottom flow from the absorption column 3 via the line 107 over the sum of the flow rate of hydrochloric acid of the bottom flow from the absorption column 3 via the line 107 and the rate of flow of hydrochloric acid in the gaseous effluent from the head of the stabilization column 3 via the line 111. The hydrochloric acid recovery ratio is generally in the range 20% to 90%. This varies as a function of the flow rate and the temperature of the washing fluid.

Advantageously, the washing fluid sent to the absorption column 3 via the lines 105 and 106 may be pre-cooled using an exchanger 8 in order to improve the hydrochloric acid recovery ratio. Preferably, washing is carried out at low temperature in order to improve the washing efficiency; more particularly, it is carried out at ambient temperature.

The washing fluid which has been used in the absorption column 3 is essentially recovered from the bottom of the absorption column 3 and is mixed, via the line 107, with the feed of hydrocarbon compounds upstream of the isomerization unit, optionally mixed with a recycled flow. The hydrochloric acid which is entrained is thereby recycled to the isomerization reaction section and further reduces the makeup of chlorinated compound which is required.

In the embodiment illustrated in FIG. 2a, the absorption unit 7 comprises a single absorption column 3. The liquid effluent obtained from the reflux drum 13 of the stabilization column 2 is injected into the absorption column 3 via the lines 125 and 126. This injection is carried out in the section of the absorption column 3 located above the washing fluid supply. It can be used to reduce the losses of hydrocarbon compounds, in particular $C_{5+}$, obtained from first contact between the gaseous effluent obtained from the drum 13 and the complementary liquid fraction of the feed of hydrocarbon compounds, and thus not capable of being recovered subsequently because the flow from the head of the absorption column 3 is then fed to a unit for the treatment of gaseous effluents (not shown in the figure) via the line 111.

In an alternative embodiment (FIG. 2b), the absorption unit 7 comprises a first absorption column 3 and a second absorption column 30. The gaseous effluent from the reflux drum 13 is sent, via the line 104, to the bottom of the absorption column 3. The complementary liquid fraction of the hydrocarbon feed is sent to the absorption column 3 via the line 106. The infeed for the complementary liquid fraction of the hydrocarbon feed is located above the infeed for the gaseous effluent from the reflux drum 13. The gaseous flow obtained from contact between the complementary liquid fraction of the hydrocarbon feed and the gaseous effluent obtained from the reflux drum 13 is recovered from the head of the absorption column 3, then is sent to a second absorption column 30 via the line 128. The liquid effluent obtained from the reflux drum 13 is sent to the absorption column 30 via the lines 125 and 126. The infeed for the liquid effluent obtained from the reflux drum 13 is located above the infeed for gaseous effluent obtained from first contact in the absorption column 3. Thus, in the second absorption column 30, a second contact is carried out between the gaseous flow obtained from first contact and the liquid effluent obtained from the reflux drum 13. The gaseous effluent obtained from second contact is recovered from the head of the absorption column 30 and is sent via the lines 111 and 124 towards the unit for treatment of gaseous effluents. The washing fluid which has been used in the absorption column 3 is essentially recovered from the bottom of the absorption columns 3 and 30.

In accordance with an essential aspect of the process of the invention, this is in effect the second contact between the gaseous effluent resulting from first contact and the liquid effluent, for example obtained from the reflux drum 13, which means that the overall yield of $C_{5+}$ can be increased and more $C_{4-}$ compounds can be liberated in the flow of the line 111.

In another alternative embodiment (not shown in the figures), the stabilization unit 20 comprises a stabilization column 2 supplied with the effluent obtained from the isomerization unit 1, and in which stabilization unit 20:
- a flow comprising the isomerate of the feed of hydrocarbon compounds is recovered from the bottom of the stabilization column 2;
- a gaseous effluent comprising at least a portion of the light compounds and the chlorinated compounds is recovered from the head of the stabilization column 2; and the gaseous effluent is sent towards an absorption unit 7;
- a liquid effluent comprising light compounds and $C_{5+}$ compounds is recovered from the stabilization column as a side stream, and the liquid effluent is sent to an absorption unit 7. The concentration of $C_{5+}$ compounds of the liquid effluent which is withdrawn as a side stream is less than the concentration of $C_{5+}$ included in the washing fluid.

As was the case with the preceding embodiments, in the stabilization unit 7, the gaseous effluent obtained from the stabilization unit 20 is brought into contact with the complementary liquid fraction of the feed of hydrocarbon compounds. The flow of vapour resulting from this first contact is subsequently brought into contact with the liquid effluent obtained from the stabilization unit 20 in order to recover the $C_{5+}$ compounds comprised in the gaseous flow resulting from first contact.

The bottom of the stabilization column 2, from which hydrochloric acid has been eliminated, constituting the product of the process (isomerate), is recovered via the line 103, and comprises one or more products enriched in high octane number compounds. This latter has a research octane number which is higher than the octane number of the feed of hydrocarbon compounds upstream of the isomerization unit. It may constitute a high octane number gasoline. A fraction of the bottom flow from the stabilization column 2 is reheated via the reboiler 11 and is sent to the bottom of said stabilization column 2.

In a preferred embodiment, the products obtained from the bottom flow from the stabilization column 2 are directed to a separation unit 4, more particularly, for example, by distillation using a distillation column 6, or indeed by adsorption. Preferably, the distillation column 6 is a deisohexaniser. As can be seen better in FIG. 2a or 2b, the deisohexaniser is a distillation column from which at least three flows are withdrawn, namely from the head via the line 108, as a side stream via the line 109, and from the bottom via the line 110.

A flow comprising products with a lower octane number than the liquid flow obtained from the stabilization column 2 (i.e. the bottom flow from the stabilization column 2) is extracted from the distillation column 6 as a side stream. These products are then preferably recycled and mixed with the fresh feed for the isomerization reaction section 1 via the line 109. The flow with a higher octane number than said liquid flow obtained from the stabilization column 2 (via the line 103) is extracted from the column head, via the line 108, and from the column bottom via the line 110.

To this end, at least a portion of the bottom flow from the stabilization column 2 is sent to a separation unit 4, for example a distillation column 6, via the line 103. The overhead flow from the column 6 is cooled via the condenser 16 and sent to the reflux drum 17. A portion of the liquid effluent obtained from the reflux drum 17 is re-injected to the head of the distillation column 6 as a reflux via a pump 14; the complementary portion of the liquid effluent obtained from the reflux drum 17 is recovered via the pump 14 and the line 108, and comprises products enriched in compounds with a high octane number. A flow which is enriched in compounds with a high octane number and refractory naphthenic $C_{6+}$ compounds is recovered from the bottom of the distillation column 6 via the line 110 in order to prevent them from accumulating. A portion of the bottom flow is reheated in a reboiler 15 and is returned to the bottom of said distillation column 6.

The products obtained from the overhead flow from the distillation column 6 essentially comprise dibranched $C_5$ and $C_6$ compounds. The products obtained from the bottom flow from the distillation column 6 essentially comprise paraffinic $C_7$ compounds, cyclohexane and naphthenes.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 14/60.090, filed Oct. 20, 2015 are incorporated by reference herein.

EXAMPLE

In the example below, a comparison was carried out between the prior art isomerization process as illustrated in FIG. 1b (and termed process 1 here) with the isomerization process of the invention as illustrated in FIG. 2a (and termed process 2 here), i.e. a process comprising a single absorption column 3 in the absorption unit 7. For the two processes, an isomerization step was carried out on a fresh feed of hydrocarbon compounds the detailed composition of which is shown in Table 1 below as percentages by weight.

TABLE 1

Composition of the fresh feed and total mass flow rate of the fresh feed at the inlet

| | | |
|---|---|---|
| Total mass flow rate | kg/h | 37 249 |
| Isobutane | % by wt | 0% |
| n-butane | % by wt | 0% |
| Isopentane | % by wt | 3% |
| n-pentane | % by wt | 27% |
| 2,2-dimethylbutane | % by wt | 1% |
| 2,3-dimethylbutane | % by wt | 3% |
| 2-methylpentane | % by wt | 15% |
| 2-methylhexane | % by wt | 12% |
| n-hexane | % by wt | 27% |
| Cyclopentane | % by wt | 2% |

TABLE 1-continued

Composition of the fresh feed and total mass
flow rate of the fresh feed at the inlet

| Methylcyclopentane | % by wt | 5% |
| Benzene | % by wt | 2% |
| Cyclohexane | % by wt | 2% |

For the two processes, the reaction section, i.e. the isomerization unit 1, was constituted by two isomerization reactors functioning in series (respectively reactor No 1 and reactor No 2), not shown in FIGS. 1 and 2. The operating conditions for the two reactors are presented below:

Inlet temperature: 120° C.;
Inlet pressure to reactor No 1: 3.5 MPa;
Inlet pressure to reactor No 2: 3.3 MPa;
Hourly space velocity: 2.2 $h^{-1}$;
Molar ratio of hydrogen to hydrocarbon: 0.1:1;
Quantity of HCl in the reactor inlet flow: 130 parts per million (ppm) by weight.

The catalyst used for the two processes in the two reactors comprised an alumina support, 7% by weight of chlorine with respect to the total weight of catalyst and 0.23% by weight of platinum with respect to the total weight of catalyst. A makeup of hydrogen was supplied to the reaction section 1 via the flow line 50; a makeup of carbon tetrachloride was supplied to the reaction section via the flow line 51.

For the two processes, the available fresh feed was mixed at 40° C. with the flow of recycled products coming from the line 109, these products essentially being compounds with a low octane number withdrawn from the deisohexaniser 6 as a side stream. After drying, the mixture was separated into two distinct flows, the first flow being directed towards the reaction section via the line 101, and the second flow (also termed the washing fluid here) being directed towards the absorption column 3 via the lines 105 and 106 and cooled to 20° C. in the exchanger 8.

The first flow, corresponding to a fraction representing 85% of the volume of the total flow of the mixture, was pumped up to 3.8 MPa, i.e. to a pressure sufficient for introduction into the isomerization reaction unit 1. The washing fluid, corresponding to a fraction representing 15% of the volume of the total flow of the mixture, was sent to the absorption column 3 after decompression to a pressure of 1.7 MPa, i.e. slightly above the operating pressure thereof.

For the process of the invention, the absorption column 3 was a packed column composed of two sections. A first section, known here as the lower section, was included between the bottom and the washing fluid supply. A second section, known here as the upper section, was included between the head of the column and the washing fluid supply. The liquid effluent obtained from the stabilization column 2 via the reflux drum 13 was injected to the head of the upper section of the absorption column 3.

For the two processes, the effluent from the isomerization reaction section was directed towards the stabilization column 2 via the line 102. The hydrochloric acid (HCl) content in the effluent was 130 parts per million (ppm) by weight.

For the two processes, the separation section 4 for the low octane number compounds consisted of a deisohexaniser 6. The bottom of the stabilization column 2 was sent to the deisohexaniser 6. The deisohexaniser 6 was in the form of a separation column the overhead products of which left via the line 108. A flow enriched in high octane number compounds and in refractory naphthenic $C_{6+}$ compounds was recovered from the bottom of the distillation column 6 via the line 110 as a purge to prevent them from accumulating.

An intermediate cut, enriched in n-hexane in particular, was removed as a side stream and was recycled to the reaction section 1 via the line 109.

Table 2 below describes the operating parameters for the series of prior art reaction units (process 1) and for the reaction units in accordance with the invention (process 2). The supply and withdrawal plates are set out in numerical order, the series of plates being numbered from the numeral one, from top to bottom. The recycle ratio for the hexanes is defined as the flow rate of fluid enriched in n-hexane obtained from the deisohexaniser recycled to the isomerization reaction section divided by the flow rate of the feed of hydrocarbon compounds as a mixture with the recycled flow located upstream of the isomerization unit.

TABLE 2

| Operating parameters | Process 1 (not in accordance) | Process 2 (invention) |
| --- | --- | --- |
| Stabilization column 2 | | |
| Number of theoretical plates | 19 | 19 |
| Operating pressure (MPa) | 1.8 | 1.6 |
| Supply plate | 7 | 7 |
| Power required in reboiler (MW) | 5.12 | 5.79 |
| Reflux ratio/Feed flow rate (by wt) | 0.35 | 0.52 |
| Deisohexaniser 4 | | |
| Number of theoretical plates | 62 | 62 |
| Operating pressure (MPa) | 0.29 | 0.29 |
| Supply plate | 20 | 20 |
| Side stream plate | 38 | 38 |
| Power required in reboiler (MW) | 14.99 | 16.30 |
| Reflux ratio/distillate | 5.05 | 5.25 |
| Hexane recycle ratio | 0.60 | 0.60 |
| Absorption column 3 of isomerization unit 7 | | |
| Number of theoretical plates | 6 | 10 |
| Operating pressure (MPa) | 1.6 | 1.4 |
| Hydrocarbon feed supply plate | 1 | 5 |
| Line 126 supply plate | N/A | 1 |
| Flow rate of liquid distillates (kg/h) | 1350 | 2100 |
| Isomerization unit 1 | | |
| Mass flow rate at reactor inlet (101 + 107) (kg/h) | 63313 | 65210 |
| HCl flow rate at reactor inlet (kg/h) | 8.2 | 8.5 |
| Carbon tetrachloride makeup flow rate (calculated as HCl equivalents) (51) (kg/h) | 3.5 | 3.5 |
| Flow rate of gas containing 75% by wt of hydrogen (50) (kg/h) | 1009 | 1006 |

The results for process 1 correspond to a process which is not on accordance with the invention (FIG. 1); the results for process 2 correspond to a process which is in accordance with the invention (FIG. 2).

The compositions of the products obtained from the flows from lines 108 and 110 are respectively summarized in Tables 3 and 4 below:

TABLE 3

Composition of flow of line 108

| | | Process 1 (not in accordance) | Process 2 (invention) |
| --- | --- | --- | --- |
| Mass flow rate | kg/h | 32937 | 33403 |
| i-pentane | % by wt | 25 | 25 |
| n-pentane | % by wt | 9 | 10 |

TABLE 3-continued

Composition of flow of line 108

| | | Process 1 (not in accordance) | Process 2 (invention) |
|---|---|---|---|
| 2,2-dimethylbutane | % by wt | 37 | 36 |
| 2,3-dimethylbutane | % by wt | 8 | 8 |
| 2-methyl-pentane | % by wt | 15 | 15 |
| 2-methyl-hexane | % by wt | 3 | 3 |
| cyclopentane | % by wt | 1 | 1 |

TABLE 4

Composition of flow of line 110

| | | Process 1 (not in accordance) | Process 2 (invention) |
|---|---|---|---|
| Mass flow rate | kg/h | 3350 | 3372 |
| n-hexane | % by wt | 5 | 5 |
| methyl-cyclopentane | % by wt | 10 | 10 |
| cyclohexane | % by wt | 53 | 54 |
| $C_{7+}$ | % by wt | 31 | 29 |

At the head of the stabilization column 2, the flow of gaseous effluent from the line 104, highly charged in hydrochloric acid, was injected into the absorption column 3 into the lower section A thereof. In accordance with the invention, the liquid distillate obtained from the reflux drum 13 of the stabilization column 2 was injected in its entirety into the upper section of the absorption column 3 via the line 126. The composition of hydrocarbon compounds obtained from the flow of line 126 is summarized in Table 5 below:

TABLE 5

Composition of hydrocarbon compounds in flow of line 126

| | | Process 2 (invention) |
|---|---|---|
| Hydrogen | % by wt | 0 |
| Methane | % by wt | 0 |
| Ethane | % by wt | 3 |
| Propane | % by wt | 16 |
| i-butane | % by wt | 61 |
| n-butane | % by wt | 14 |
| i-pentane | % by wt | 5 |
| n-pentane | % by wt | 1 |
| $C_{6+}$ | % by wt | 0 |
| HCl | ppm by wt | 450 |

Two flows were obtained from the absorption column 3, namely a bottom flow essentially corresponding to washing fluid, enriched in hydrochloric acid and re-entrained light compounds which was sent to the isomerization unit 1 via the line 107, and from the head of the absorber 3 a gaseous effluent depleted in hydrochloric acid which was sent to the treatment unit (not shown in the figures) via the line 111.

The composition of the gaseous effluent obtained from the absorption column 3 via the line 111 is presented in Table 6 below:

TABLE 6

Composition of flow of line 111 (gaseous effluent from absorption column 3)

| | | Process 1 (not in accordance) | Process 2 (invention) |
|---|---|---|---|
| Total mass flow rate | kg/h | 639 | 1483 |
| HCl flow rate | kg/h | 2.8 | 3.5 |
| Hydrogen | % by wt | 13 | 6 |
| Methane | % by wt | 29 | 13 |
| Ethane | % by wt | 35 | 18 |
| Propane | % by wt | 1 | 18 |
| i-butane | % by wt | 1 | 38 |
| n-butane | % by wt | 1 | 6 |
| i-pentane | % by wt | 1 | 1 |
| n-pentane | % by wt | 7 | 0 |
| $C_{6+}$ | % by wt | 12 | 0 |
| HCl | ppm by wt | 4426 | 2376 |

It will be observed that the content of $C_{5+}$ in the gaseous effluent from the absorption column 3 obtained from the line 111 was very substantially reduced in the process of the invention (Example 2) compared with the prior art (Example 1).

Table 7 below describes the composition of the total effluent sent to the treatment unit via the line 124, corresponding to the overhead gaseous flow obtained from the absorption column 3 via the line 111 and to the vaporized liquid effluent 123, this latter being zero in the example of the invention.

TABLE 7

Composition of flow of line 124 (vapour effluent)

| | | Process 1 (not in accordance) | Process 2 (invention) |
|---|---|---|---|
| Mass flow rate | kg/h | 1975 | 1483 |
| HCl flow rate | kg/h | 3.5 | 3.5 |
| Hydrogen | % by wt | 4 | 6 |
| Methane | % by wt | 9 | 13 |
| Ethane | % by wt | 13 | 18 |
| Propane | % by wt | 14 | 18 |
| i-butane | % by wt | 30 | 38 |
| n-butane | % by wt | 7 | 6 |
| i-pentane | % by wt | 12 | 1 |
| n-pentane | % by wt | 4 | 0 |
| $C_{6+}$ | % by wt | 6 | 0 |
| HCl | ppm by wt | 1795 | 2376 |

It will be observed that the flow rate of HCl recovered in the vapour effluent obtained from the line 124 is identical in the process of the invention and in the prior art process, i.e. 3.5 kg/h. In addition, for an identical HCl recovery flow rate for the process 1 (not in accordance) and process 2 (in accordance with the invention), the mass flow rate of the flow of line 124 is lower in process 2 than in process 1, since the vapour effluent from line 124 of process 2 comprises very few $C_{5+}$ compounds (only 1% by weight of i-pentane). Thus, for an identical recycle ratio, with a reduced mass flow rate in the context of process 2, the concentration of HCl is higher in the context of process 2 than in the context of process 1.

Table 8 below describes the yield and properties of the products obtained from the isomerization process which are constituted by the mixture of flows obtained from lines 108 and 110. The yield is defined as the ratio between the mass flow rate of the sum of the flows obtained from lines 108 and 110 over the flow rate of the feed of hydrocarbon compounds in the line 100 upstream of the isomerization unit, optionally mixed with a recycled flow.

TABLE 8

Properties and yield of products obtained from isomerization process constituted by the mixture of flows obtained from lines 108 and 110

|  | Process 1 (not in accordance) | Process 2 (invention) |
| --- | --- | --- |
| Octane number (RON) | 87.4 | 87.4 |
| Reid vapour pressure (MPa) | 0.082 | 0.082 |
| Yield | 97.4 | 98.7 |

For a final product obtained with the same Reid vapour pressure and the same octane number, the process of the invention can be used to significantly improve the overall reaction yield. For an identical level of recovery of chlorinated compounds, the process of the invention can be used to improve the yield of the isomerization process by forming high octane number products.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the isomerization of a feed of hydrocarbon compounds comprising $C_5$ and/or $C_6$ hydrocarbon compounds, said process comprising a loop for recycling at least one chlorinated compound which has the following steps:
   a) supplying an isomerization unit (1) with at least one portion of said feed of hydrocarbon compounds and isomerizing said at least one portion in the presence of a chlorinated catalyst;
   b) supplying a stabilization unit (20) comprising at least one stabilization column (2) with the effluent obtained from the isomerization unit (1) and separating said effluent into:
      a gaseous effluent comprising at least one chlorinated compound;
      a liquid effluent comprising a concentration $C_A$ of $C_5+$ compounds; and
      a liquid flow comprising at least one isomerate of the feed of hydrocarbon compounds;
   c) providing an absorption unit (7) comprising an absorption column (3), wherein the absorption comprises:
      a first contact between the gaseous effluent obtained from step b) and a washing fluid, said washing fluid being selected from a portion of said feed of hydrocarbon compounds and/or at least a portion of said liquid flow comprising at least one isomerate of the feed of hydrocarbon compounds obtained from step b), wherein said washing fluid comprises a concentration $C_B$ of $C_5+$ compounds, with $C_A<C_B$;
      a second contact between the gaseous flow resulting from said first contact and said liquid effluent obtained from step b);
   wherein in said absorption column (3), said gaseous effluent from step b) is supplied to the absorption column (3) below said washing fluid, and said liquid effluent from step b) is supplied to the head of the absorption column (3) above said washing fluid;
   d) extracting a liquid flow enriched in chlorinated compounds from the absorption unit (7) and recycling the liquid flow to the isomerization unit (1); and
   e) extracting said liquid flow comprising at least one isomerate of the feed of hydrocarbon compounds from the stabilization unit (20).

2. The process according to claim 1, wherein the liquid flow comprising at least one isomerate of the feed of hydrocarbon compounds of step e) undergoes a separation in a separation unit (4) in order to obtain at least one flow with a higher octane number than said liquid flow of step e) and at least one flow with a lower octane number than said liquid flow of step e).

3. The process according to claim 2, wherein at least a portion of the flow with a lower octane number than said liquid flow of step e) is recycled to the absorption unit (7) as washing fluid.

4. The process according to claim 2, wherein at least a portion of the flow with a lower octane number than said liquid flow of step e) is recycled upstream of the isomerization unit (1), said recycled flow being mixed with the feed of hydrocarbon compounds.

5. The process according to claim 1, wherein said feed of hydrocarbon compounds, optionally as a mixture with said liquid flow comprising at least one isomerate of the feed of hydrocarbon compounds obtained from step b), is dried upstream of the isomerization unit (1) and the absorption unit (7).

6. The process according to claim 1, wherein the washing fluid is cooled upstream of the absorption unit (7).

7. The process according to claim 1, wherein when the washing fluid is a portion of said feed, the flow rate of said portion of said feed is in the range 5% to 50% by volume of the total flow of said feed.

8. The process according to claim 1, wherein the concentration of $C_{4-}$ compounds comprised in the liquid effluent obtained in step b) is more than 15% by weight.

9. The process according to claim 1, wherein the gaseous flow obtained from the second contact in the absorption unit (7) is extracted and treated in a unit for the treatment of gaseous effluents.

10. The process according to claim 1, wherein a portion of the liquid effluent obtained from step b) is vaporized and then sent directly to a unit for the treatment of gaseous effluents.

11. The process according to claim 1, wherein step a) is carried out at a temperature in the range 100° C. to 300° C., at a pressure in the range 0.2 to 3.5 MPa, with a hydrogen/hydrocarbons molar ratio in the range 0.1:1 to 1:1 and with a space velocity in the range 0.5 to 10 $h^{-1}$.

12. The process according to claim 1, wherein step a) is carried out in the presence of a chlorinated catalyst comprising an alumina support and a metal from group VIII.

13. The process according to claim 12, wherein the catalyst comprises 2% to 10% by weight of chlorine with respect to the total catalyst weight, and 0.1% to 0.40% by weight of platinum with respect to the total catalyst weight.

* * * * *